United States Patent [19]

Gowing

[11] Patent Number: 5,509,294
[45] Date of Patent: Apr. 23, 1996

[54] APPARATUS FOR DETERMINING AMOUNT OF GASES DISSOLVED IN LIQUIDS

[75] Inventor: Scott Gowing, Gaithersburg, Md.

[73] Assignee: The United States of America as represented by the Secretary of the Navy, Washington, D.C.

[21] Appl. No.: 416,561

[22] Filed: Apr. 4, 1995

Related U.S. Application Data

[62] Division of Ser. No. 677,941, Apr. 1, 1991, Pat. No. 5,442,948.

[51] Int. Cl.⁶ .................................................. G01N 7/14
[52] U.S. Cl. ........................... 73/19.05; 73/19.12; 96/193
[58] Field of Search ............................. 73/19.01, 19.05, 73/19.06, 19.1, 19.12, 19.09; 95/266, 241, 247; 96/193

[56] References Cited

U.S. PATENT DOCUMENTS

| | | | |
|---|---|---|---|
| 2,138,141 | 11/1938 | Cromer et al. | 73/19.05 |
| 3,731,530 | 5/1973 | Tanguy et al. | 73/19.01 X |
| 4,117,727 | 10/1978 | Friswell et al. | 73/19.02 |
| 4,329,869 | 5/1982 | Toda | 73/19.1 |
| 4,700,561 | 10/1987 | Dougherty | 73/19.05 |

*Primary Examiner*—Michael J. Brock
*Attorney, Agent, or Firm*—Howard Kaiser

[57] ABSTRACT

The quantity of gases dissolved in liquids is determined by introducing a liquid sample into a hollow cylinder with a plunger, retracting the plunger to create a void space into which gases originally dissolved in the liquid sample diffuse, compressing the gases into a reduced volume, measuring the absolute pressure of the gases, and calculating the amount of gases originally dissolved in the liquid from the absolute pressure, the temperature, the vapor pressure of the liquid at the prevailing temperature, the volumes of liquid and the final volume of the gas, by using the ideal gas law.

16 Claims, 1 Drawing Sheet

APPARATUS FOR DETERMINING AMOUNT OF GASES DISSOLVED IN LIQUIDS

The invention described herein may be manufactured and used by or for the Government of the United States of America for governmental purposes without the payment of any royalties thereon or therefor.

This application is a division of patent application Ser. No. 07/677,941, filed Apr. 1, 1991, U.S. Pat. No. 5,442,948, issued Aug. 22, 1995.

BACKGROUND OF THE INVENTION

This invention relates to apparatus and method for determining the amount of gases (such as oxygen, nitrogen, carbon dioxide and carbon monoxide) dissolved in liquids (such as water or samples of blood). More particularly, this invention relates to apparatus which, unlike most conventional apparatus used for such determinations, does not employ liquid mercury, which is toxic and represents a health hazard.

A variety of apparatus for determining the amount of gases dissolved or entrapped in liquids is known to the art.

A device referred to as the Van Slyke apparatus for determining the amount of gases dissolved in liquids has been commercially available for many years. It employs a sample chamber, a shutoff valve, a mercury manometer and a mercury reservoir acting as a sealing fluid and as a means of producing vacuum.

U.S. Pat. No. 2,138,141 describes apparatus for determining the amount of gas contained in drilling mud used in drilling oil and gas wells. It employs a sample cylinder with a shutoff valve and piston and a Bourdon-type of pressure gauge protected by a metal diaphragm.

U.S. Pat. No. 2,680,060 describes a device embodying the features of the Van Slyke apparatus referred to above employing mercury as a sealing fluid and further employing a cylinder with a plunger to adjust the level of the mercury in the apparatus.

U.S. Pat. No. 3,171,722 describes a device resembling that of U.S. Pat. No. 2,680,060 above, used for injecting a gas sample into a gas chromatograph.

U.S. Pat. No. 4,315,890 relates to a sample tube for liquids having volatile components dissolved therein, and also having a reagent supported on an inert support such as glass wool in a portion of the sample tube, for indicating qualitatively by change in color whether certain volatile components, such as ethanol, are present in the sample liquid.

U.S. Pat. No. 4,607,342 describes a device for determining the quantity of carbon dioxide dissolved in carbonated beverages comprising a computer which controls solenoid-operated valves for admitting a sample of the beverage into a test chamber, stirring it to release carbon dioxide, measuring the pressure in the chamber, and automatically computing therefrom the level of carbonation of the beverage.

U.S. Pat. No. 4,745,794 describes functionally similar apparatus for determining the level of carbonation of beverages.

British Patent 2,190,196 describes apparatus for determining the quantity of gases dissolved in liquids comprising a conical flask having a side neck for a movable piston and a center neck for a pressure transducer.

SUMMARY OF THE INVENTION

Incorporated herein by reference is copending patent application Ser. No. 07/677,941, filed Apr. 1, 1991, entitled "Method for Determining Amount of Gases Dissolved in Liquids," now U.S. Pat. No. 5,442,948. An object of the invention disclosed therein is to provide method of determining the quantity of gases dissolved in liquids which is convenient and which can be carried out by individuals with modest skills in chemical laboratory procedures. The method of the invention disclosed therein involves introduction of a liquid sample into the cylinder, the positioning of the plunger in three predetermined positions, and taking a pressure reading, from which the quantity of dissolved gases may be calculated.

It is an object of the present invention to provide apparatus for determining the quantity of gases dissolved in liquids which is more economical than apparatus now known and which does not require the use of mercury, a potential health and safety hazard in laboratories.

The apparatus of the present invention comprises a hollow cylinder with a plunger slidably disposed therein and a pressure transducer.

DESCRIPTION OF THE PREFERRED EMBODIMENT OF THE INVENTION

Figure 1:
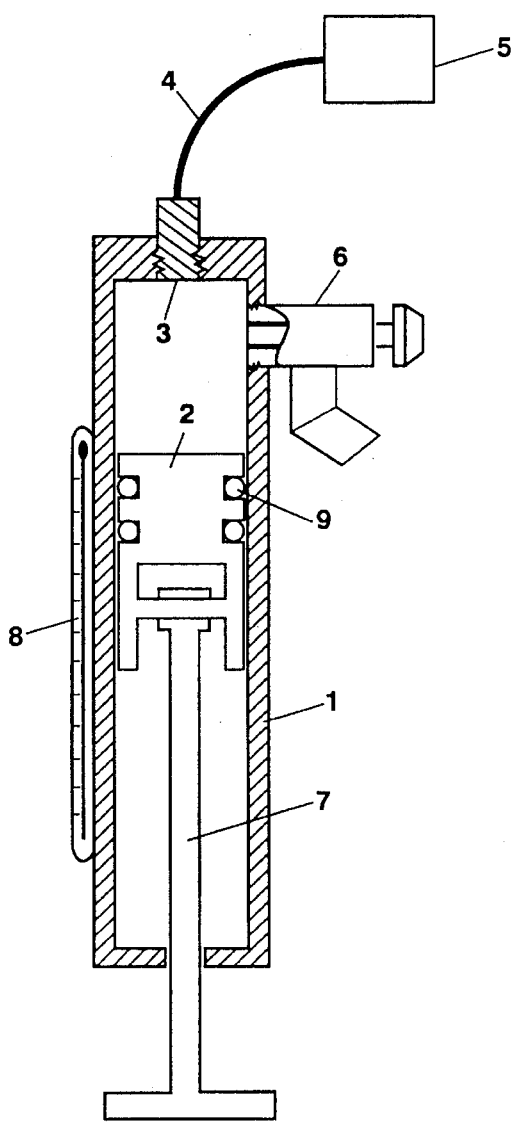
FIG. 1 is a cross-section of the preferred embodiment of this invention.

With reference to FIG. 1, within an elongated hollow cylinder 1 having an open end and a closed end is provided a snugly fitting cylindrical plunger 2 capable of sliding back and forth in the cylinder in an axial direction. The plunger forms a gas-tight and liquid-tight seal along its periphery and the inside surface of the cylinder.

Figure 2:
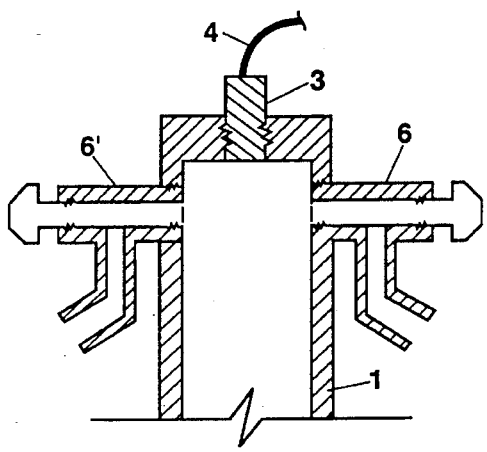
FIG. 2 is a modification of the embodiment.

Near the closed end of the cylinder there is provided a tight-shutoff valve 6, which is connected to the cylinder and whose purpose is to admit liquid into the cylinder and to expel gas and liquid therefrom. Optionally, as illustrated in FIG. 2, two such shutoff valves 6 and 6' may be provided, one for admitting liquid into the cylinder, and the other one for draining such liquid or for expelling gas.

Also provided near the closed end of the cylinder is a pressure transducer 3, whose output is transmitted to a pressure indicator 5. Preferably, the pressure transducer comprises four strain gauges securely fastened to a metal diaphragm and exposed to the interior of the cylinder (not shown). The strain gauges are connected by electrical wiring 4 to the pressure indicator 5. The four strain gauges, connected in a Wheatstone bridge circuit (not illustrated), have electrical resistances which vary in response to variation in pressure exerted upon the metal diaphragm by the gas pressure in the cylinder.

A supply voltage is provided across the input terminals of the Wheatstone bridge. Across the output terminals of the Wheatstone bridge, there will appear a voltage signal which is directly related to the absolute pressure of the gas in the cylinder. This output voltage is amplified as needed and displayed by a voltmeter, which may be calibrated in units of absolute pressure.

The pressure transducer as described, or its equivalent, is well known in the art. A pressure transucer of the type having a metal diaphragm with strain gauges produces a negligble volume displacement as the metal diaphragm flexes in response to changes in pressure. The volume of the cylinder, which must be accurately known for accurate determinations of the amounts of dissolved gases, thus is virtually unaffected by the pressure inside the cylinder.

Figure 3:
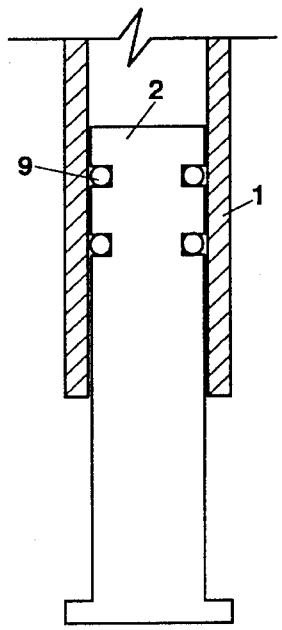
FIG. 3 illustrates a modification of the plunger.

To the plunger 2, there may be attached a handle 7, as shown in FIG. 1, to facilitate moving the plunger back and forth in the cylinder bore. Alternatively, the plunger may be a solid cylindrical body which can be manipulated without a separate handle, as shown in FIG. 3. Calibrated volume markings may be provided on the stem of the plunger or on the handle as appropriate.

Gas-tightness and liquid-tightness around the periphery of the plunger in the cylinder may be assured by O-rings 9 fitted into circumferential grooves in the peripheral surface of the plunger, with the O-rings slidably bearing against the smooth inside wall of the cylinder.

A thermometer 8, such as a mercury-in-glass thermometer, may be strapped to the outside of the cylinder to indicate the temperature of the cylinder. Alternatively, the junction of a thermocouple (not illustrated) may be attached to the outside of the cylinder, with electrical wires connected to a potentiometer whose voltgage reading is directly related to the temperature of the cylinder.

The cylinder and plunger preferably are made of steel, stainless steel, brass, aluminum, or glass.

The method of determining the quantity of gases dissolved in a liquid is described as follows:

(I) Initially, the cylinder is set up with the closed end up and the plunger end down. A predetermined volume of sample liquid is introduced into the cylinder by first expelling the air from the cylinder through the open shutoff valve by displacement of the plunger toward the closed end; then drawing an excess of liquid into the cylinder by dipping the outlet of the open shutoff valve into the liquid and pulling the plunger away from the closed end of the cylinder; and finally expelling excess liquid and entrapped gas or air bubbles by moving the plunger to a predetermined point inscribed on the plunger handle, and closing the shutoff valve. The sample volume, typically, is 10 ml.

Alternatively, when two valves are employed as illustrated in FIG. 2, both valves are opened simultaneously to allow sample liquid to flow through the volume in the cylinder, the sample liquid being pumped by external means. After all air has been expelled from the cylinder volume, both valves are closed.

(II) The plunger is retracted so as to create a volume much larger than that of the liquid, whereby a void volume under vacuum is created above the liquid and into which gases originally dissolved in the liquid sample diffuse. Typically, the void volume thus created should be from five to ten times the volume of the liquid sample to insure virtually complete diffusion of the dissolved gases into the void volume. Also diffusing into the void volume will be vapors of the constituents of the liquid, such as water, each constituent of the liquid attaining a partial pressure commensurate with its vapor pressure, its concentration in the liquid and its activity coefficient.

(III) The apparatus is now turned into a horizontal position to allow the sample liquid to spread out and expose a large surface to maximize the rate of diffusion of dissolved gases into the void volume. The plunger is held in its position until the pressure indicator gives a constant reading, indicating that the gases originally dissolved in the liquid have disengaged therefrom and reached equilibrium within the expanded volume.

(IV) The cylinder is returned to its original position and the plunger is moved toward the closed end of the cylinder so as to compress the gases, the volume of the cylinder being less than that in steps (II) and (III) but greater than the volume of the liquid. The cylinder volume, typically, is 12 ml, the gas volume 2 ml, and the liquid volume 10 ml.

(V) The absolute pressure is read on the pressure indicator.

The quantity of gases dissolved in the liquid is now calculated from the ideal gas law:

$$n = \frac{(P - P_V)V_{gas}}{(RTV_{liq})},$$

where
 $n$=gram-moles of gas dissolved per ml of liquid
 $P$=pressure reading in cylinder, atm.
 $P_v$=vapor pressure of liquid constituents, atm., at sample temperature
 $V_{gas}$=gas volume in cylinder, typically 2 ml
 $R$=universal gas constant, 82.06 atm-ml/gram-moles/deg K
 $T$=absolute temperature, deg K, or deg C+273
 $V_{liq}$=liquid volume, typically 10 ml Other modifications of this invention will be apparent to those skilled in the art, all falling within the scope of the invention as described herein and claimed in the following.

What is claimed is:

1. Apparatus for determining the amount of gas which is dissolved in liquid, comprising:

a hollow member having a vertical cylindrical body, a closed upper end, an open lower end, and at least one port, said cylindrical body being substantially symmetrical with respect to the longitudinal axis of said member, each said port being located in said cylindrical body near said closed upper end;

at least one shutoff valve, each said shutoff valve corresponding to a different said port, said member having a capacity which is fluid-tight when every said port is closed;

a piston device which enters said member through said open lower end and is movable, slidably and fluid-tightly with respect to the inside surface of said cylindrical body, in the direction of said axis, so as to decrease said capacity when said piston device is moved upward and increase said capacity when said piston device is moved downward;

whereby said member may be caused to exclusively contain a selected volume of liquid and a selected volume of gas, said selected volume of gas filling the upper portion of said capacity and said selected volume of liquid filling the lower portion of said capacity, said selected volume of gas consisting essentially of gas which has been dissolved in and has diffused from said selected volume of liquid; and a device which is coupled with said closed upper end, said device approximately aligned with said axis and disposed to measuring the absolute pressure of said selected volume of gas.

2. Apparatus for determining the amount of gas dissolved in a liquid, comprising:

a hollow cylinder which is normally placed in the vertical position whereby said hollow cylinder has a closed top end and an open bottom end and at least one port, each said port located near said closed end;

at least one valvular passage, each said valvular passage associated with a different said port, said at least one valvular passage being for introducing liquid into, and removing liquid and gas from, said cylinder;

a plunger having a periphery which forms a fluid-tight seal and is slidable with respect to the inside surface of said cylinder, said plunger entering said cylinder through said open end;

a transducer for producing a signal corresponding to absolute pressure within said cylinder, said transducer located within said cylinder and closely joined at said closed end;

electrical wiring;

an indicator of said absolute pressure, said indicator connected by said electrical wiring to said transducer and located outside said cylinder.

3. Apparatus for determining the amount of gas as in claim 2, wherein said fluid-tight seal includes a plurality of O-rings attached at said periphery of said plunger.

4. Apparatus for determining the amount of gas as in claim 2, wherein:

said transducer includes a plurality of strain gauges;

said strain gauges are secured to a metal diaphragm;

said strain gauges are connected in a Wheatstone bridge circuit;

said strain gauges are responsive to variations of exerted pressure upon said metal diaphragm in accordance with variations of said absolute pressure;

a supply voltage is applied to the input terminals of said Wheatstone bridge circuit; and an output voltage related to the absolute pressure in said cylinder is generated.

5. Apparatus for determining the amount of gas as in claim 4, including means for amplifying said output voltage.

6. Apparatus for determining the amount of gas as in claim 4, wherein said electrical wiring provides means for transmitting said output voltage to said indicator.

7. Apparatus for determining the amount of gas as in claim 6, wherein said indicator is a voltmeter.

8. Apparatus for determining the amount of gas as in claim 7, wherein said voltmeter is calibrated in units of absolute pressure.

9. Apparatus for determining the amount of gas as in claim 2, wherein said cylinder and plunger are made of material selected from the group of materials consisting of steel, stainless steel, brass, aluminum and glass.

10. Apparatus for determining the amount of gas as in claim 2, wherein:

said plunger permits slidable movement, while at least one said valvular passage is open and said cylinder is placed vertically, so as to introduce into said cylinder a selected volume of liquid and to remove from said cylinder gas which is not dissolved in said selected volume of liquid;

said plunger permits slidable movement, while every said valvular passage is closed and said cylinder is placed vertically, so as to create within said cylinder a void above said selected volume of liquid;

said cylinder permits horizontal positioning, so as to promote diffusion into said void of said gas which is dissolved in said selected volume of liquid; and said plunger permits slidable movement, while every said valvular passage is closed and said cylinder is placed vertically, so as to compress into a selected volume of gas said gas which diffuses into said void.

11. Apparatus for determining the amount of gas as in claim 10, wherein:

said plunger permits slidable movement upward, so as to expel from said cylinder gas which is not dissolved in said selected volume of liquid;

said plunger permits slidable movement downward, so as to draw said liquid into said cylinder; and said plunger permits slidable movement upward, so as to expel excess liquid and entrapped gas.

12. Apparatus for determining the amount of gas as in claim 10, wherein said at least one said valvular conduit which is open is two valvular conduits, and wherein when both said valvular conduits are open, said valvular conduits permit pumping of liquid into said cylinder through one said valvular conduit, so as to expel excess liquid and entrapped gas through the other said valvular conduit.

13. Apparatus for determining the amount of gaseous matter which is dissolved in liquid matter, comprising:

a vertical cylindroid container which has a sealed upper end, an apertured lower end, and a passage which is proximate said sealed upper end;

a shutoff valve for said passage;

a plunger which enters said container through said apertured lower end, said plunger being downwardly movable for increasing the capacity within said container and upwardly movable for decreasing the capacity within said container;

a device which is centrally mounted to said sealed upper end within said container, said device being for measuring the absolute pressure of gaseous matter which is adjacently below said sealed upper end, said gaseous matter occupying the upper portion of said capacity and having diffused from said liquid matter occupying the lower portion of said capacity.

14. Apparatus for determining the amount of gaseous matter as in claim 13, wherein said shutoff valve permits admission of liquid matter into said container and removal of liquid matter and gaseous matter from said container.

15. Apparatus for determining the amount of gaseous matter as in claim 13, wherein said passage is a first passage and said shutoff valve is a first shutoff valve, and further comprising a second passage and a second shutoff valve, said second shutoff valve being proximate said sealed upper end and for said second passage, said first shutoff valve permitting admission of liquid matter into said container and said second shutoff valve permitting removal of liquid matter and gaseous matter from said container.

16. Apparatus for determining the amount of gaseous matter as in claim 13, wherein said device is a transducer and wherein said apparatus further comprises an indicator which electrically engages said transducer.

\* \* \* \* \*